(12) United States Patent
Roncucci et al.

(10) Patent No.: US 7,749,991 B2
(45) Date of Patent: Jul. 6, 2010

(54) SUBSTITUTED METAL-PHTHALOCYANINES, THEIR PREPARATION AND THE USE THEREOF

(75) Inventors: Gabrio Roncucci, Colle Val d'Elsa (IT); Lia Fantetti, Florence (IT); Maria Paola De Filippis, Florence (IT); Donata Dei, San Gimignano (IT); Giulio Jori, Padua (IT)

(73) Assignee: L. Molteni & C. Dei Fratelli Alitti-Societa di Esercizio S.p.A., Scandicci (IT)

( * ) Notice: Subject to any disclaimer, the term of this patent is extended or adjusted under 35 U.S.C. 154(b) by 337 days.

(21) Appl. No.: 11/600,055

(22) Filed: Nov. 16, 2006

(65) Prior Publication Data

US 2007/0066513 A1 Mar. 22, 2007

Related U.S. Application Data

(62) Division of application No. 10/311,663, filed on Dec. 16, 2002, now Pat. No. 7,144,879.

(51) Int. Cl.
*C07B 47/00* (2006.01)
*C07D 487/22* (2006.01)
*A01N 55/02* (2006.01)

(52) U.S. Cl. .................................. 514/185; 540/145
(58) Field of Classification Search .................. 540/145; 514/185
See application file for complete search history.

(56) References Cited

FOREIGN PATENT DOCUMENTS

EP 0 906 758 A1 4/1999

OTHER PUBLICATIONS

Gaspard, "A New Method for the Synthesis of Zinc Tetrakis-(3-methylpyridyloxy)-phthalocyanine and the Physical Properties of Dimers Formed by Complexation of the Cationic Phthalocyanine with Anionic Porphyrins," J. Chem. Soc. Perkin Trans. II, 383-389 (1989).
Siegl, "Metal-Chelating 1,3-bis(2'-Pyridylimino)isoindolines," J. Heterocyclic Chem., 18:1613-1618 (1981).
Wöhrle et al., "A Simple Synthesis of 4,5-Disubstituted 1,2-Dicyanobenzenes and 2,3,9,10,16,17,23,24-Octasubstituted Phthalocyanines," Synthesis, 2:194-196 (1993).
Kaninskii et al., "Substitution of the Nitro Group in 4-Nitrophthalonitrile with the Phenol-Metal Carbonate System as Nucleophile," Journal of Organic Chemistry of the USSR, 38:964-967 (1992).
Mikhalenko et al., "Phthalocyanines and Related Compounds. XIX. Tetra- and Octaamino- Substituted Phthalocyanines," Journal of Chemistry, 51(7):1405-1411 (1981).
Haworth et al., "Some Green Pigments of the Phthalocyanine Series," Chemical Abstracts, 39(20), Abstract No. 4610 (1945).
Freccero et al., "Photochemical Reaction of Phthalimides and Dicyanophthalimides with Benzylic Donors," J. Org. Chem., 58:1740-1745 (1993).
Gracheva et al., "Preparation of 1,2,3,4-tetrahydroquinoline Derivatives," Caplus Online Chemical Abstracts Service, Abstract No. 108:204512 (1987).
Ben-Hur et al., "The Phthalocyanines: A New Class of Mammalian Cells Photosensitizers With a Potential for Cancer Phototherapy," *Int. J. Radiat. Biol.*, 47(2):145-147 (1985).
Gomer, "Photodynamic Therapy in the Treatment of Malignancies," *Seminars in Hematology*, 26(1):27-34 (1989).
Jori, "Tumour Photosensitizers: Approaches to Enhance the Selectivity and Efficiency of Photodynamic Therapy," *J. Photochem. Photobiol. B: Biology*, 36:87-93 (1996).
Brasseur et al., "Biological Activities of Phthalocyanines—V. Photodynamic Therapy of EMT-6 Mammary Tumors in Mice With Sulfonated Phthalocyanines," *Photochem. Photobiol.*, 45(5):581-586 (1987).
Brassuer et al., "Biological Activities of Phthalocyanines—VII. Photoinactivation of V-79 Chinese Hamster Cells by Selectively Sulfonated Gallium Phthalocyanines," *Photochem. Photobiol.*, 46(5):739-744 (1987).
Paquette et al., "Biological Activities of Phthalocyanines—VIII. Cellular Distribution in V-79 Chinese Hamster Cells and Phototoxicity of Selectively Sulfonated Aluminum Phthalocyanines," *Photochem. Photobiol.*, 47(2):215-230 (1988).
Brasseur et al., "Biological Activities of Phthalocyanines—IX. Photosensitization of V-79 Chinese Hamster Cells and EMT-6 Mouse Mammary Tumor by Selectively Sulfonated Zinc Phthalocyanines," *Photochem. Photobiol.*, 47(5):705-711 (1988).
Margaron et al., "Structure-Photodynamic Activity Relationships of a Series of 4-Substituted Zinc Phthalocyanines," *Photochem. Phitobiol.*, 63(2):217-223 (1996).
Paquette et al., "Phthalocyanines Pour la Thérapie Photocynamique du Cancer: Effet des Substituants Tertio-Butyles sur l'accumulation cellulaire et l'activité Photodynamique de Phthalocyanines Sulfonées de Gallium," *J. Chim. Phys.*, 88:1113-1123 (1991).

*Primary Examiner*—James O. Wilson
*Assistant Examiner*—Paul V. Ward
(74) *Attorney, Agent, or Firm*—Nixon Peabody LLP

(57) ABSTRACT

The present invention is directed to metal-phthalocyanines of general formula (I) to the corresponding conjugates, the processes for their preparation and use in the photodynamic therapy of microbial infections (viral, bacterial and mycotic), tumor, pre-cancerous and proliferative pathologies and/or in the diagnosis, as well as for blood and blood derivatives sterilization.

12 Claims, 3 Drawing Sheets

SUBSTITUTED METAL-PHTHALOCYANINES, THEIR PREPARATION AND THE USE THEREOF

This application is a Divisional of prior application Ser. No. 10/311,663 filed Dec. 16, 2002 now U.S. Pat. No. 7,144,879.

FIELD OF THE INVENTION

The present invention refers to metal-phthalocyanines of formula (I) hereafter reported, which are photosensitizer compounds of therapeutic use, characterised by absorption and fluorescence in the red region of the visible spectrum. Said compounds are useful for the treatment and diagnosis of various infectious diseases and of diseases characterised by cellular hyperproliferation, in particular tumours, psoriasis, actinic keratosis, atheromas, endoarterial hyperplasia and prostate hyperplasia; said compounds are useful as well for blood and blood derivatives sterilisation.

STATE OF THE ART

Organic molecules containing the chromofluorophore macrocycle of the phthalocyanine are known to produce reactive derivatives of oxygen, in particular singlet oxygen or radicals, by interacting with visible light.

Compounds having a basic phthalocyanine structure are used in therapy, for example in photodynamic therapy (PDT) and/or for diagnostic purposes (E. Ben-Hur and I. Rosenthal, *Int. J. Radiat. Biol.*, Vol. 47, pp. 145-147, 1985).

Other photosensitising agents having applications in photodynamic therapy (PDT) and diagnosis are Zn(II)-phthalocyanines and the conjugates thereof described in the European patent application No. EP 98115036 in the name of the Applicant.

Even though the research in this field has made a lot of progress and photosensitising products defined as "second generation products" have been synthesised, their therapeutic application is still limited since their efficacy against pathogenic agents or tumour cells is not sufficiently high or selective.

Up to today, the main therapeutic application of photosensitising molecules is associated with their anticancer activity and is based on the use of porphyrin photosensitising agents (Gomer C. J., *Seminars in Hematology*, Vol. 26, pp. 27-34, 1989), which, albeit giving promising results in palliative or curative treatment of different neoplasms, are markedly limited by low efficacy and selectivity and have prolonged persistence in the skin which may cause phenomena of generalised photosensitivity (Jori G., *J. Photochem. Photobiol., B: Biol.*, Vol. 36, pp. 87-93, 1996).

The non-optimal distribution of first generation photosensitizers are due to the poor selectivity, which is related to their physical-chemical features.

It is therefore evident the importance of developing derivatives suitable for therapeutic and diagnostic applications, as the phthalocyanine compounds described in the present invention.

The main characteristics, which makes phthalocyanine derivatives suitable for therapy and/or diagnostic purposes in vivo, are the following:

i) low dark toxicity, high quantum yield in singlet oxygen production and/or a high fluorescence quantum yield;

ii) capability of being activated by red or near infrared light, radiations able to penetrate deeply into tissues;

iii) presence of substituents having suitable photodynamic and physical-chemical features, among which only one substituent bears a reactive or potentially activatable functional group, allowing the site-specific conjugation of the photosensitive molecule to macromolecular carriers if required.

iv) sufficient solubility in water for a good bioavailability, fast metabolism and a preservation of the biologic properties of the conjugated macromolecular carrier.

In addition to the above mentioned characteristics, it has been recently disclosed in scientific literature that the number and charge of substituents effect the in vitro and in vivo phototoxicity of the compounds (Brasseur et al., *Photochem. Photobiol.*, vol. 45, pp. 581-586, 1987; Brasseur et al., *Photochem Photobiol.*, vol. 47, pp. 705-711, 1988).

In particular, the highest phototoxicity has been shown when two adjacent sulphonic groups are present, which has been related to an increased capacity of penetration into the tumour cells membrane (Brasseur et al., *Photochem. Photobiol.*, vol. 46, pp. 739-744, 1987; Paquette et al., vol. 47, pp. 215-220, 1988; Margaron et al., *Photochem Photobiol.*, vol. 62, pp. 217-223, 1996).

It has been moreover proved that the addition of hydrophobic groups to sulphonated phthalocyanines generates an increase of the amphiphilic properties, a higher cellular uptake and a greater photocytotoxicity (Paquette et al., *J. Chim. Phys.*, vol. 88, pp. 1113-1123, 1991).

SUMMARY OF THE INVENTION

In spite of what reported in the above cited literature about the studies on structures for photosensitising agents showing photocytotoxic properties, and from which it comes out that an optimal uptake occurs when two strong anionic groups are present on adjacent rings of the macrocycle so to form an amphiphilic molecule with a hydrophobic matrix, the Applicant has surprisingly found that phthalocyanines substituted in specific positions of only one ring of the macrocycle with cationic groups or with protonable groups, are particularly active, and are particularly effective in inducing the in vitro photoinactivation.

Object of the present invention, are therefore the metal-phthalocyanines of general formula (I)

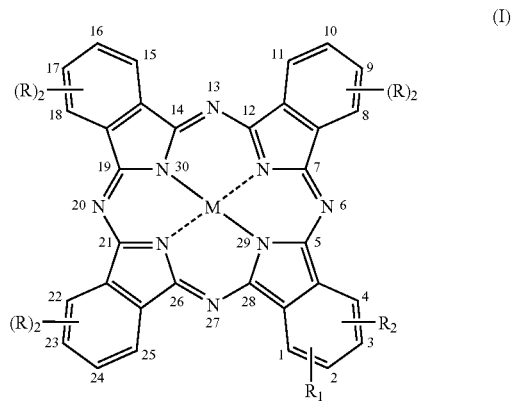

in which:

M is chosen in the group consisting of Zn, $Si(OR_8)_2$, $Ge(OR_8)_2$ and $AlOR_8$;

R is H or a group selected from alkyl, alkenyl and alkyloxy group, linear or branched, having from 1 to 10 carbon atoms provided that, when R is different from H, the positions 8, 11, 15, 18, 22, 25 or 9, 10, 16, 17, 23, 24 are substituted; and $R_1$ and $R_2$, equal or different from one another, are H or a cationic group or a protonable group, provided that when $R_1$ and $R_2$ are the same, they are not H and are in the positions 1,4 or 2,3, whereas, when only one between $R_1$ and $R_2$ is different from H, the position 1 or 2 is substituted, or $R_1$ and $R_2$, taken together, form a saturated or unsaturated heterocycle, possibly substituted, which may contain up to two heteroatoms chosen in the group consisting of N, O and S;

$R_8$ is chosen from between H and C1-C15 alkyl, and their pharmaceutically acceptable salts.

Further object of the present invention are the above formula (I) compounds site-specifically conjugated with bioorganic carriers, such as aminoacids, polypeptides, proteins and polysaccharides.

Said compounds of formula (I), as well as the corresponding conjugates, are useful for the treatment of microbial infections (viral, bacterial and mycotic), tumour, pre-cancerous and proliferative pathologies in photodynamic therapy, and are analogously useful as diagnostic agents for the identification of pathologically affected areas as well as for the photodynamic sterilisation of blood and blood derivatives.

Features and advantages of compounds of formula (I) according to the present invention will be illustrated in detail in the following description.

—■— indicates the curve obtained by using the compound 20 prepared as described in Example 3.

—●— indicates the curve obtained by using the compound 19 prepared as described in Example 3.

...▽... shows the curve obtained by using the compound PPC as reported by Minnoch A. et al. *J. Photochem. Photobiol.* 32: 159-164 (1996).

—▼— shows the curve obtained by using the compound identified as Compound 42 in the European Patent Application No. 98115036.0 in the name of the Applicant.

...□... shows the curve obtained by using Zn phtalocyanine commercialised by Aldrich.

...○... shows the curve obtained by using the compound T$_4$MPyP as reported by Merchat M. et al. *J. Photochem. Photobiol.* 32: 153-157 (1996).

Figure 3:
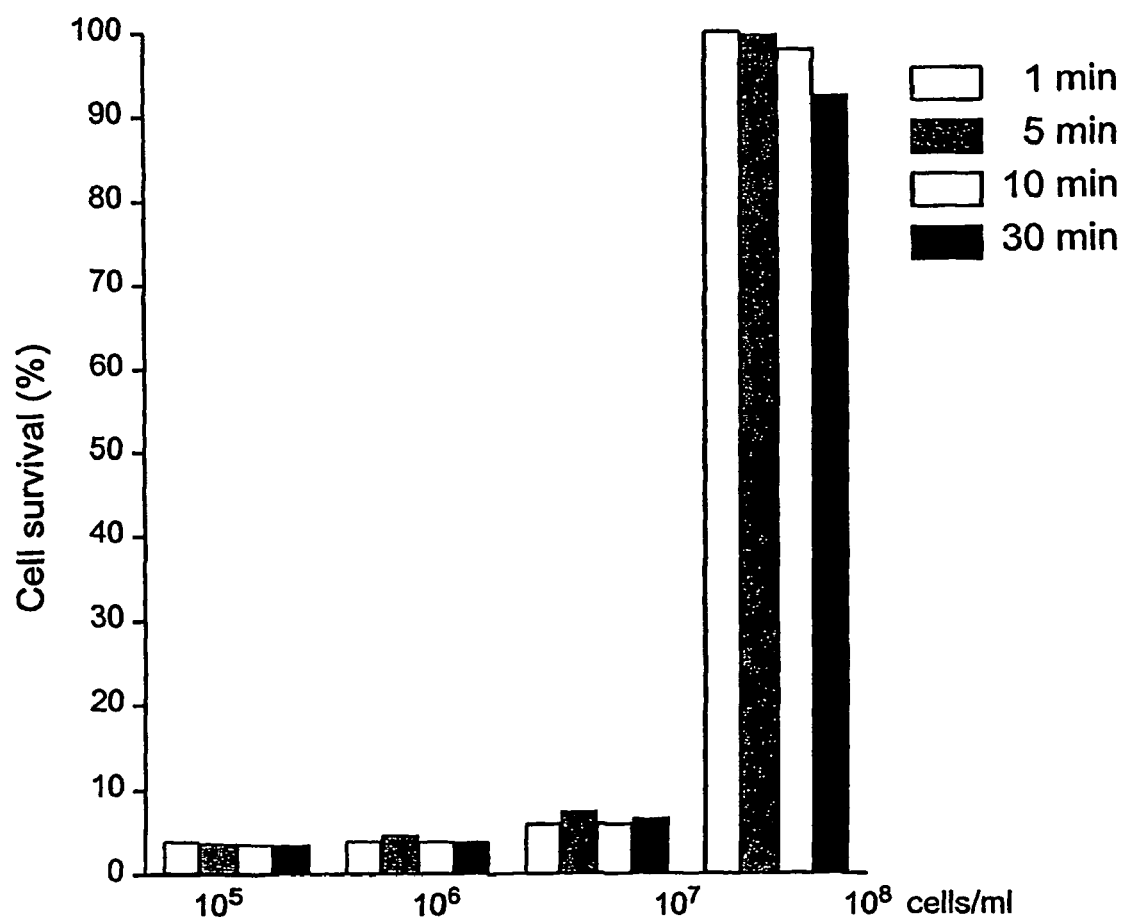

FIG. 3: shows the variation of CFU for different concentrations of *Candida albicans* cells, incubated for 60 min. with 1 μM of the compound 19 prepared as described in Example 3, then irradiated with 100 mW/cm$^2$ light. On the y-axis cells survival (%) is reported.

DETAILED DESCRIPTION OF THE INVENTION

The present invention makes it possible to meet the above mentioned requirements thanks to the metal-phthalocyanines of general formula (I).

According to the present invention Zn(II)-phthalocyanines are preferred.

Compounds having formula (I) according to the present invention bear the same substituents in specific positions on the three benzo-rings of the phthalocyanine nucleus, which are different from the forth one bearing at least one cationic group or a protonable group.

By protonable group according to the above general formula (I) an aminic group is preferably meant.

According to a preferred embodiment of the present invention, when one substituent between $R_1$ and $R_2$ is H, the other one is $(X)_pR_3$, wherein X is chosen in the group consisting of O, S, —NR$_6$ and —CH$_2$—; and $R_3$ is $$(Y)_m \!\!-\!\! \left( Z \!\!\left\langle \begin{array}{c} (R_4)_n \\ (R_5)_w \\ (R_6)_t \\ (R_7)_u \end{array} \right. \right)_v$$

where:

Y is chosen in the group consisting of C1-10 alkyl and phenyl, possibly substituted, or it forms with the Z group, to which it is bound, a saturated or unsaturated heterocycle, possibly substituted, which may contain up to two heteroatoms chosen in the group consisting of N, O and S;

Z is chosen in the group consisting of —N, —CH$_2$N and —CONHCH$_2$CH$_2$N;

$R_4$ and $R_5$, equal or different from one another, are chosen in the group consisting of C1-15 alkyl and phenyl, or form with the Z group, to which they are bound, a saturated or unsaturated heterocycle, possibly substituted, which may contain up to two heteroatoms chosen in the group consisting of N, O and S;

$R_6$ and $R_7$, equal or different from one another, are chosen in the group consisting of H and C1-C15 alkyl;

m, n, p, w, t and u, independently from one another, are 0 or 1; and v is an integer comprised between 1 and 3.

By saturated or unsaturated heterocycle possibly substituted, as defined in the above general formula, the following are preferably meant: morpholine, piperidine, pyridine, pyrimidine, piperazine, pyrrolidine, pyrroline, imidazole, aniline, and julolidine (2,3,6,7-tetrahydro-1H,5H benzo[ij]quinolizine).

According to the invention, the preferred products are those in which the group $(X)_pR_3$ contains substituents bearing tertiary or quaternary nitrogen.

In particular, the said group $(X)_pR_3$ is preferably represented by:

-continued

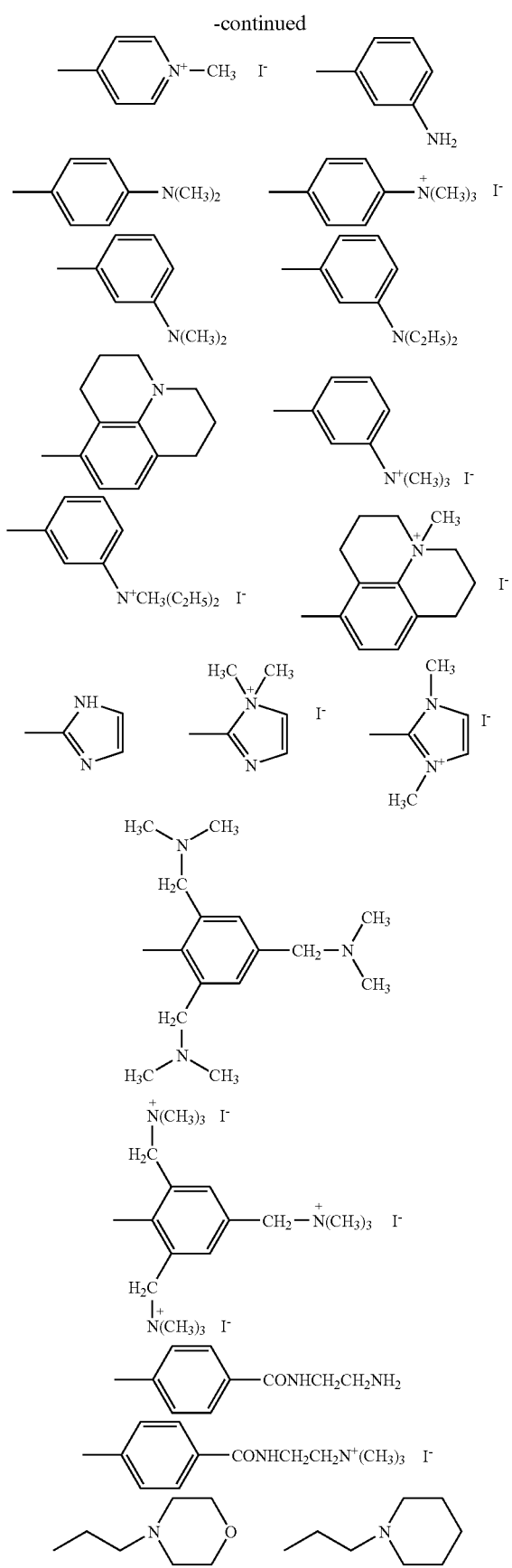
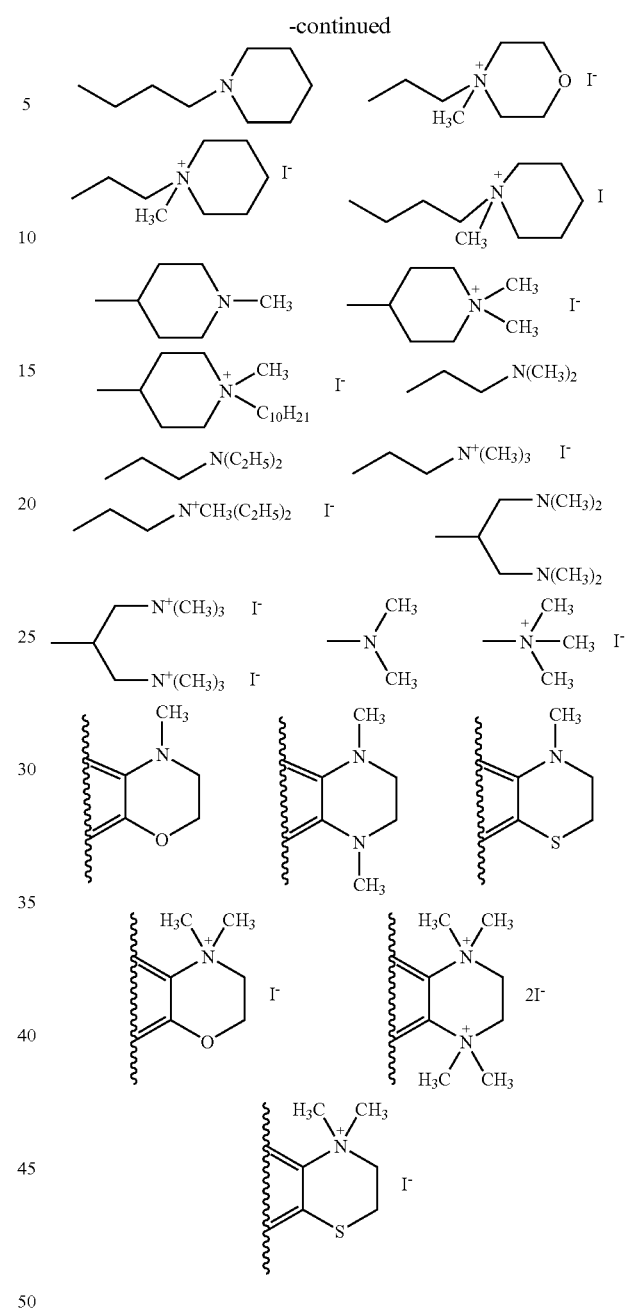

The present compounds show valuable photodynamic characteristics making them useful in photodynamic therapy (PDT) against bacterial, fungal and viral infections, for various hyperproliferative diseases as well as for photosterilization of blood and blood derivatives such as platelets and erythrocytes. In this particular case the present compounds can be added directly, or previously bound to suitable matrix, to blood or blood derivatives, according to the known techniques and thereafter irradiated. Moreover they can be used as diagnostic agents for the identification of pathologically affected areas.

The present products possess a molar absorption coefficient higher than the photosensitising agents presently used in therapy, which represents an important requirement for an effective therapeutic response.

These products may be activated by tissue penetrating radiation having a wavelength longer than 650 nm, and hence are suitable for the PDT against diseases, both dermatological and internal.

The products formed by photobleaching of those compounds are non toxic. This finding reinforces their usefulness as therapeutics since after having exploited their action the compounds are inactivated by the light and then are no more potentially toxic in vivo.

The present compounds are active in the singlet oxygen production or allow the production of reactive species of oxygen under conditions of poor oxygenation. Such requirement is particularly important because it allows to treat specifically anaerobic microorganisms or tumour cells, well-known characterised by an environment poor of oxygen.

In particular, the exemplified products possess very high efficiency for micro-organisms such as yeast fungi and mycoplasma, Gram-positive and Gram-negative bacteria, showing the capability of specific localisation on micro-organisms compared to the mammalian host cells.

The finding about differential toxicity between host cells and micro-organisms strengthen the importance of the claimed products (I).

The present invention comprises also the above described formula (I) compounds site-specifically conjugated with a bio-organic carrier able to direct the molecule to a definite target.

The carrier is usually chosen among molecules having well-known specific binding capacities, for example aminoacids (preferably basic aminoacids), polypeptides, (preferably consisting of basic aminoacids), proteins and polysaccharides normally used for targeting purposes.

The binding phthalocyanine(I)/carrier may occur for example between the related amino or carboxyl group, or may occur involving other specific functional groups on the phthalocyanine moiety or on the carrier molecule.

Functional groups such as thiol, maleimide derivatives, α-bromo esters and amides, diazonium salts and azido derivatives can be introduced following current to procedures in order to pre-functionalise both the phthalocyanine or the carrier depending upon the selected carrier itself and its stability.

The compounds of the present invention can be prepared, by condensation in the homogeneous as well as in the heterogeneous phase of phthalonitriles properly substituted, according to reaction schemes known in organic chemistry.

For example, the amino substituted Zn(II)-phthalocyanines of formula (I) can be prepared according to the herein described processes.

a) Liquid phase by mixed condensation method using two different 1,2-benzenedicarbodinitriles, having suitable substituents, defined by the following formula (II) and formula (III)

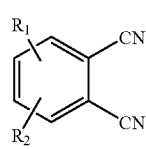

(II)

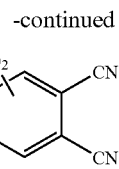

(III)

wherein R, $R_1$ and $R_2$ are as defined above. In the formula (II) compound, when $R_1$ and $R_2$ are the same, the positions 3,6 or 4,5 are substituted, whereas, when one substituent between $R_1$ and $R_2$ is H, the other one is in the position 3 or 4. In the formula (III) compound, when R is different from H, the positions 3,6 or 4,5 are substituted.

The phthalonitriles of formula (II) and (III) are mixed in different ratios (1:1 to 1:6) by using neat 1,8-diazabicyclo-[5.4.0]-undec-7-ene (DBU), or with solvent (dichloromethane, methanol, N,N-dimethylformamide), in the presence of anhydrous zinc(II) acetate at various temperatures and reaction times, to afford a mixture of compounds. The mixture is first purified by extensive washing steps with water and organic solvents (i.e. precipitation DMF/water, extractions water/organic solvent) and then by chromatography (i.e. by using silica gel, deactivated basic or neutral aluminium oxide, Sephadex) followed by further washings of the separated products with organic solvents ($Et_2O$, AcOEt, $CH_2Cl_2$, $CHCl_3$, acetone, methanol).

b) Solid Phase

Some of the phthalocyanines of formula (I), having suitable substituents, can also be prepared by solid phase synthesis with the aim at avoiding the time-consuming difficult purification procedures foreseen by the statistical synthesis. The preparation process, starting from a dinitrile bound to a solid phase reacted with a differently substituted dinitrile previously transformed into diaminoisoindolyl derivative, has already been disclosed [*Tetrahedron Letters*, vol. 23 (30) pp. 3023-3026 (1982); *J. Org. Chem.*, vol. 56, pp. 82-90 (1991)]; however, the described procedure is a refinement of the above cited one and specifically leads to amino substituted metal phthalocyanines never reported so far.

Cationic metal phthalocyanines of formula (I) can be prepared by reacting the corresponding neutral compounds obtained as described above with an excess of neat alkyl iodide, or in the presence of a suitable solvent (i.e. N-Methyl-2-pyrrolidinone, DMF, methanol, chloroform), at temperature comprised between room temperature and reflux for a reaction time comprised between 1 hour and 10 days). The crude products can be generally purified by several washings with various organic solvents, such as $Et_2O$, $CH_2Cl_2$, and $CHCl_3$, ethyl acetate or acetone.

Each prepared compound can be identified by means of various spectroscopic techniques as $^1$H-NMR and $^{13}$C-NMR, MS and spectrophotometrically characterised in the UV-Vis region.

Hereinafter the preparation of specific compounds of formula (I) is reported for better illustrating the invention.

EXAMPLE 1

Synthesis of the Compound of Formula (I) in which M is Zn, R=$R_2$=H and $R_1$=1,3-bis-(dimethylamino)-2-propyloxy in the Position 2 (Compound 1)

0.272 g of 4-[1,3-bis-(dimethylamino)-2-propyloxy]-1,2-benzene dicarbodinitrile (1 mmol) and 0.384 g of 1,2-benzenedicarbodinitrile (3 mmol) are dissolved in a little amount of methanol and added of Zn(OAc)$_2$ (0.176 g; 0.96 mmol) and DBU (0.66 ml; 0.42 mmol). The mixture is heated at 150° C., under an inert atmosphere, for 3 h and 30 min. The blue mixture is dissolved in DMF and precipitated with basic water several times, then is purified by flash-chromatography on silica gel, eluting with Et$_2$O/DMF (4:1), EtOAc/DMF (4:1), EtOAc/DMF (1:1), EtOAc/DMF (1:2), DMF. The product of interest is further purified by Washing with Et$_2$O and acetone. Blue-violet powder.

UV-vis (DMF) $\lambda_{max}$ ($\epsilon$, M$^{-1}$cm$^{-1}$) 344, 606, 672 (2.7635×10$^5$).

$^1$H NMR (DMSO-d$_6$) $\delta$ ppm 9.42-9.30 (m, 6H), 9.23 (d, 1H), 8.95 (s, 1H), 8.30-8.20 (m, 6H), 7.90-7.80 (m, 1H), 5.25-5.18 (m, 1H), 2.90 (d, 4H), 2.49 (s, 12H).

ESI-MS, m/z

Using the above described procedure, the following products were obtained:

Compound 2: compound of formula (I) in which M is Zn, R=R$_2$=H and R$_1$=pyridin-4-yl-oxy in the position 2; blue-violet powder; UV-vis (DMF) $\lambda_{max}$, nm ($\epsilon$, M$^{-1}$cm$^{-1}$) 350, 606, 674 (8.9670×10$^4$). $^1$H NMR (DMSO-d$_6$) $\delta$ ppm 9.40-8.95 (m, 7H), 8.62 (d, J=7.50 Hz, 2H), 8.35-8.10 (m, 8H), 6.59 (d, J=7.43 Hz, 2H). ESI-MS, m/z 670 [M+H]$^+$.

Compound 3: compound of formula (I) in which M is Zn, R=R$_2$=H and R$_1$=3-(dimethylamino)phenoxy in the position 2; blue-violet powder. UV-vis (DMF) $\lambda_{max}$, nm 346, 605, 671. $^1$H NMR (DMSOd$_6$) $\delta$ ppm 9.48-9.05 (m, 7H), 8.72-8.65 (m, 1H), 8.32-8.12 (m, 6H), 7.90-7.80 (m, 1H), 7.52-7.38 (m, 1H), 6.88-6.75 (m, 3H), 3.08 (s, 6H). ESI-MS, m/z 712.3 [M$^+$H]$^+$.

Compound 4: compound of formula (I) in which M is Zn, R=R$_2$=H and R$_1$=1-methylpiperidin-4-yl-oxy in the position 2; blue-violet powder. UV-vis (DMF) $\lambda_{max}$, nm 343, 606, 673. $^1$H NMR (DMSO-d$_6$) $\delta$ ppm 9.45-9.30 (m, 5H), 9.17 (d, J=8.51 Hz, 1H), 8.794 (d, J=1.7 Hz, 1H), 8.33-8.18 (m, 7H), 7.775 (dd, J=8.21 Hz, J=2.1 Hz, 1H), 5.20-4.98 (m, 1H), 2.95-2.80 (m, 2H), 2.60-2.40 (m, 2H), 2.40-2.12 (m, 2H; s, 3H), 2.15-1.94 (m, 2H). ESI-MS, m/z 690.2 [M$^+$H]$^+$.

Compound 5: compound of formula (I) in which M is Zn, R=H and R$_1$=R$_2$=pyridin-4-yl-oxy in the positions 2,3; blue-violet powder. UV-vis (DMF) $\lambda_{max}$, nm 347, 666, 684. $^1$H NMR (DMSO-d$_6$) $\delta$ ppm 9.43-9.39 (m, 6H), 8.30-8.22 (m, 8H), 8.12 (d, J=7.6 Hz, 4H), 6.39 (d, J=7.6 Hz, 4H).

Compound 6: compound of formula (I) in which M is Zn, R=R$_2$=H and R$_1$=1,3-bis-(dimethylamino)-2-propyloxy in the position 1; blue-violet powder. UV-vis (DMF) $\lambda_{max}$ nm 336, 611, 677. $^1$H NMR (DMSO-d$_6$) $\delta$ ppm 9.50-9.42 (m, 6H), 9.07 (bd, J=7.33 Hz, 1H), 8.40-8.12 (m, 7H), 7.91 (bd, 7.95, 1H), 5.50-5.38 (m, 1H), 3.25-3.17 (m, 4H), 2.47 (s, 12H).

Compound 7: compound of formula (I) in which M is Zn, R=H, and R$_1$=R$_2$=3-(piperidin-1-yl)propyloxy in the positions 1,4; blue-green powder. UV-vis (DMF) $\lambda_{max}$, nm 335, 622, 690. $^1$H NMR (DMSO-d$_6$) $\delta$ ppm 9.45-9.35 (m, 6H), 8.27-8.18 (m, 6H), 7.72 (s, 2H), 4.76-4.71 (m, 4H), 3.10-3.03 (m, 4H), 2.57-2.51 (m, 12H), 1.63-1.36 (m, 12H). FAB-MS, m/z 861 [M$^+$H]$^+$.

Compound 8: compound of formula (I) in which M is Zn, R=H and R$_1$=R$_2$=3-(dimethylamino)phenoxy in the positions 2,3; blue-violet powder. UV-vis (DMF) $\lambda_{max}$ 344, 606, 672. $^1$H NMR (DMSO-d$_6$) $\delta$ ppm 9.39-9.28 (m, 6H), 8.95 (s, 2H), 8.20-8.15 (m, 6H), 7.45-7.35 (m, 4H), 6.72-6.73 (m, 4H), 3.03 (s, 12H).

Compound 9: compound of formula (I) in which M is Zn, R=R$_2$=H and R$_1$=pyridin-2-yl-oxy in the position 2; blue-violet powder. UV-vis (DMF) $\lambda_{max}$, nm 343, 606, 672. $^1$H NMR (DMSO-d$_6$) $\delta$ ppm 9.38-9.11 (m 7H), 8.50-8.40 (m, 1H), 8.32-8.07 (m, 9H), 7.88-7.75 (m, 1H), 6.85-4.68 (m, 1H).

Compound 10: compound of formula (I) in which M is Zn, R=R$_2$=H and R$_1$=pyridin-3-yl-oxy in the position 2; blue-violet powder. UV-vis (DMF) $\lambda_{max}$, nm 343, 606, 672. $^1$H NMR (DMSO-d$_6$) $\delta$ ppm 9.40-8.85 (m, 8H), 8.72-8.62 (m, 1H), 8.34-8.10 (m, 7H), 8.09-7.95 (m, 1H), 7.94-7.68 (m, 2H).

Compound 11: compound of formula (I) in which M is Zn, R=R$_2$=H and R$_1$=3-(dimethylamino)phenoxy in the position 1; blue-violet powder. UV-vis (DMF) $\lambda_{max}$, nm 333, 607, 674. $^1$H NMR (DMSO-d$_6$) $\delta$ ppm 9.48-9.28 (m, 6H), 9.23 (d, J=7.46 Hz, 1H), 9.99 (d, J=7.26 Hz, 1H), 8.38-8.11 (m, 7H), 7.81 (d, J=7.65 Hz, 1H), 7.14 (dd, J$_1$=J$_2$=8.40 Hz, 1H), 7.10-7.00 (m, 1H), 6.53 (bd, J=8.40 Hz, 1H).

Compound 12: compound of formula (I) in which M is Zn, R=H and R$_1$=R$_2$=2-(diethylamino)ethylthio in the positions 2,3; blue-violet powder. UV-vis (DMF) $\lambda_{max}$ 347, 612, 680. $^1$H NMR (DMSO-d$_6$) $\delta$ ppm 9.28-9.17 (m, 6H), 8.85 (s, 2H), 8.26-8.15 (m, 6H), 3.59-3.52 (bt, 4H), 3.07-3.00 (bt, 4H), 2.79 (q, J=7 Hz, 8H), 1.20 (t, J=7 Hz, 12H).

Compound 13: compound of formula (I) in which M is Zn, R=H and R$_1$=R$_2$=pyridin-3-yl-oxy in the positions 2,3; blue-violet powder. UV-vis (DMF) $\lambda_{max}$ 346, 605, 671. $^1$H NMR (DMSO-d$_6$) $\delta$ ppm 9.10-9.32 (m, 6H), 8.77 (bs, 2H), 8.55 (d, J$_1$=4.6 Hz, 2H), 8.25-8.18 (m, 8H), 7.87 (bd, J$_2$=8.3, 2H), 7.61 (dd, J$_1$=4.6 Hz, J$_2$=8.3, 2H).

Compound 14: compound of formula (I) in which M is Zn, R=R$_2$=H and R$_1$=2-(dimethylamino)ethyloxy in the position 1; blue-violet powder. UV-vis (DMF) $\lambda_{max}$ 334, 611, 677. $^1$H NMR (DMSO-d$_6$) $\delta$ ppm 9.36 (m, 8H), 8.95 (d, J=7.5 Hz, 1H), 8.23 (m, 7H), 8.12 (dd, J$_1$=7.7 Hz, J$_2$=7.5 Hz, 1H), 7.75 (d, J=7.7 Hz, 1H), 4.83 (bt, 2H), 2.62 (s, 6H).

Compound 15: compound of formula (I) in which M is Zn, R=R$_2$=H and R$_1$=2-(piperidin-1-yl)ethyloxy in the position 1; blue-violet powder. UV-vis (DMF) $\lambda_{max}$ 337, 611, 677. $^1$H NMR (DMSO-d$_6$) $\delta$ ppm 9.30-9.27 (m, 8H), 8.83 (d, J=7.6 Hz, 1H), 8.22-8.19 (m, 7H), 8.04 (dd, J$_1$=J$_2$=7.6 Hz, 1H), 7.66 (d, J=7.6 Hz, 1H), 4.82 (bt, 2H), 2.88 (bt, 2H), 2.52 (m, 4H), 1.64-1.47 (m, 6H).

Compound 16: compound of formula (I) in which M is Zn, R=R$_2$=H and R$_1$=2-(piperidin-1-yl)ethyloxy in the position 2; blue-violet powder. UV-vis (DMF) $\lambda_{max}$ 347, 607, 671. $^1$H NMR (DMSO-d$_6$) $\delta$ ppm 9.30-9.23 (m, 8H), 8.99 (D, J=8.4, 1H), 8.61 (bs, 1H), 8.25-8.17 (m, 7H), 7.63 (d, J=8.4 Hz, 1H), 4.61 (bt, 2H), 3.03 (bt, 2H) 2.70 (m, 4H), 1.68-1.53 (m, 6H).

EXAMPLE 2

Synthesis of the Compound of Formula (I) in which M is Zn, R=R$_2$=H and R$_1$=N-(2-aminoethyl)benzamidoyl-4-oxy trifluoro acetate (Compound 17)

a) Functionalization of the Polystyrene-Based Resin with the Phthalodinitrile 159 mg (0.078 mmol) of diaminoethane-trityl resin (0.49 mmol/g) are swollen in 12.5 mL of DMF. To this suspension 282 mg (0.78 mmol) of the succinimide ester of the 4(3',4'-dicyano)phenoxybenzoic acid are added, and the product is kept under stirring at room temperature for 18 hours. The liquid phase is removed from the resin by vacuum filtration, and the resin is washed several times with small volumes of DMF, CH$_2$Cl$_2$ and MeOH.

b) Solid-Phase Condensation Reaction 100 mg (0.78 mmol) of 1,2-dicyanobenzene are dissolved in 2 ml of DMF, the obtained functionalised resin (0.078 mmol) is added to this solution and the mixture warmed for one hour at 50° C. Then 79 mg (0.43 mmol) of zinc(II)acetate and 0.322 ml (2.15 mmol) of DBU are added and the suspension is heated up to 160° C. for 4 hours, under stirring and nitrogen atmosphere. After cooling at room temperature, the two phases are separated by vacuum filtration, and the solid phase is washed with MeOH and DMF.

c) Separation of the Zn-Phthalocyanine from the Resin

The green-blue resin is suspended in a solution of trifluoroacetic acid (TFA) (375 ml, 5%) and tri-isopropyl silane (TIS) (375 ml, 5%) in $CH_2Cl_2$ (7.5 ml) and kept in this solution for 1.5 hours. The two phases are then separated by vacuum filtration and the resin is washed with $CH_2Cl_2$ and with small volumes of DMF and MeOH alternatively until the solution is colourless. The filtrate is concentrated and the blue-green residue purified by column chromatography and by washing with solvents to give 8 mg of the desired product 2-7[N-(2-aminoethyl)benzamidoyl-4-oxy]zinc(II)phthalocyanine trifluoro acetate (Compound 17); green-blue solid; UV-vis (DMF) $\lambda_{max}$, nm; $^1$H-NMR (DMSOd$_6$), δ ppm 9.6-9.3 (m, 7H), 9.0-8.75 (s, 1H), 8.75-8.6 (m, 1H, disappeared with $D_2O$), 8.35-8.2 (m, 6H), 8.2-7.9 (m, 6H, modified with $D_2O$), 7.6-7.4 (m, 2H), 3.7-3.5 (m, 2H), 3.2-3.0 (m, 2H), ESI-MS, m/z: 755 [M$^+$H]$^+$.

EXAMPLE 3

Synthesis of the Compound of Formula (I) in which M is Zn, R=R$_2$=H and R$_1$=1,3-bis-(trimethylammonium)-2-propyloxy diiodide in the Position 2 (Compound 18)

10 mg of Compound 1 prepared as described above in Example 1, (0.014 mmol) is dissolved in 2.5 ml of N-Methyl-2-pyrrolidinone and treated with an excess of MeI, leaving the reaction mixture at r.t. for 15 h. The product is precipitated with Et$_2$O from the mixture, recovered by filtration and purified by several washings of the precipitate with organic solvents, thus obtaining the desired product 2[1,3-bis-(trimethylammonium)-2-propyloxy]zinc(II)phtalocyanine diiodide; blue powder. UV-vis (DMF) $\lambda_{max}$ (ε, M$^{-1}$cm$^{-1}$) 343, 607, 672 (1.9275×10$^5$). $^1$H NMR (DMSO-d$_6$) δ ppm 9.55-9.40 (m, 7H), 9.23 (s, 1H), 8.42-8.35 (m, 6H), 8.25-8.15 (m, 1H), 6.30-6.10 (m, 1H), 4.45-4.10 (m, 4H), 3.55 (s, 18H). ESI-MS, m/z 375.3 [M−2I]$^{2+}$.

Using the above described procedure, the following products were also obtained:

Compound 19: compound of formula (I) in which M is Zn, R=R$_2$=H and R$_1$=3-(trimethylammonium)phenoxy iodide in the position 2; UV-vis (DMF) $\lambda_{max}$, nm (ε, M$^{-1}$ cm$^{-1}$) 345, 606, 671 (1.7073×10$^5$). $^1$H NMR (DMSO-d$_6$) δ ppm 9.55-9.42 (m, 5H), 9.42-9.35 (m, 1H), 9.05-8.97 (m, 1H), 8.38-8.20 (m, 8H), 8.05-7.80 (m, 3H), 7.68-7.60 (m, 1H), 3.77 (s, 9H). ESI-MS, m/z 726.4 [M−I]$^+$ Compound 20: compound of formula (I) in which M is Zn, R=R$_2$=H and R$_1$=1,1-dimethylpiperidinium-4-yl-oxy iodide in the position 2. UV-vis (DMF) $\lambda_{max}$, nm (ε, M$^{-1}$cm$^{-1}$) 341, 606, 671 (1.8197×10$^5$). $^1$H NMR (DMSO-d$_6$) δ ppm 9.52-9.39 (m, 5H), 9.35 (d, 1H), 9.00 (d, 1H), 8.40-8.25 (m, 7H), 7.95 (dd, 1H).2. ESI-MS, m/z 704.3 [M−I]$^+$ Compound 21: compound of formula (I) in which M is Zn, R=H and R$_1$=R$_2$=3-(1-methylpiperidinium-1-yl)propyloxy iodide in the positions 1,4; blue-green powder. UV-vis (DMF) $\lambda_{max}$, nm 337, 619, 687. $^1$H NMR (DMSO-d$_6$) δ ppm 9.48-9.39 (m, 6H), 8.31-8.27 (m, 6H), 7.89 (s, 2H), 5.10-4.90 (m, 4H), 4.13-4.03 (m, 4H), 3.55-3.45 (m, 8H), 3.23 (s, 6H), 2.90-2.65 (m, 4H), 1.90-1.72 (m, 8H), 1.68-1.32 (m, 4H). ESI-MS, m/z 1015.4 [M−I]$^+$, 444.6 [M−2I]$^{2+}$.

Compound 22: compound of formula (I) in which M is Zn, R H and R$_1$=R$_2$=3-(trimethylammonium)phenoxy iodide in the positions 2,3; blue powder. UV-vis (DMF) $\lambda_{max}$, nm 342, 606, 672. $^1$H NMR (DMSO-d$_6$) δ ppm 9.52-9.38 (m, 6H), 9.30 (s, 2H), 8.45-8.30 (m, 6H), 8.12 (bs, 2H), 7.92-7.80 (m, 4H), 7.63-7.58 (bd, 2H), 3.73 (18H).

Compound 23: compound of formula (I) in which M is Zn, R=R$_2$=H and R$_1$=1,3-bis-(trimethylammonium)-2-propyloxy diiodide in the position 1; green powder. UV-vis (DMF) $\lambda_{max}$, nm 334, 609, 676. $^1$H NMR (DMSO-d$_6$) δ ppm 9.60-9.38 (m, 6H), 9.36-9.30 (m, 1H), 8.52-8.20 (m, 7H), 7.95-7.85 (m, 1H), 6.40-6.30 (m, 1H), 4.68-4.38 (m, 4H), 3.44 (s, 18H). ESI-MS, m/z 1005 [M+H]$^+$.

Compound 24: compound of formula (I) in which M is Zn, R=R$_2$=H and R$_1$=3-(trimethylammonium)phenoxy iodide in the position 1; blue-violet powder. UV-vis (DMF) $\lambda_{max}$, nm 333, 607, 674. $^1$H NMR (DMSO-d$_6$) δ ppm 9.50-9.30 (m, 6H), 8.78-8.70 (m, 1H), 8.52 (bs, 1H), 8.4-8.06 (m, 7H), 8.02-7.92 (m, 1H), 7.72-7.65 (m, 1H), 7.60-7.50 (m, 1H), 7.26-7.34 (m, 1H), 3.80 (s, 9H). ESI-MS, m/z 726.3 [M−I]$^+$.

Compound 25: compound of formula (I) in which M is Zn, R=H and R$_1$=R$_2$=2-(diethylmethylammonium)ethylthio iodide in the positions 2,3; blue-violet powder. UV-vis (DMF), $\lambda_{max}$, nm 347, 611, 681. $^1$H NMR (DMSO-d$_6$) δ ppm 9.49-9.45 (m, 8H), 8.36-8.31 (m, 6H), 4.11-4.05 (m, 4H), 3.85-3.69 (m, 4H), 3.55-3.65 (bq, 8H), 3.25 (s, 6H), 1.42 (t, J=7 Hz, 12H).

Compound 26: compound of formula (I) in which M is Zn, R=R$_2$=H and R$_1$=1-methylpyridinium-4-yl-oxy in the position 2; blue-violet powder, UV-vis (DMF) $\lambda_{max}$, nm (ε, M$^{-1}$cm$^{-1}$) 350, 606, 674. $^1$H NMR (DMSO-d$_6$) δ ppm 9.85-9.68 (bd, 2H), 9.42 (bs, 1H), 9.41-9.00 (m, 7H), 8.52-8.41 (bd, 1H), 8.40-8.02 (m, 8H). ESI-MS, m/z 684.2 [M−I]$^+$.

EXAMPLE 4

Preparation of the Conjugate Between Compound 17 and Bovine Serum Albumin (BSA)

Bovine serum albumin (BSA) has been prepared as a 5 mg/ml solution concentration in PBS (pH 8.5); the Compound 17, obtained as described above in Example 2, has been prepared as DMSO solution (5 mg/ml).

In one experiment, 12.5 equivalents of compound 17 are mixed with 200 μl of BSA solution; the blue suspension is maintained under gentle stirring at 4° C. then 12.5 equiv. of disuccinimidylsuberate (DSS, Pierce) are slowly added and the temperature raised to room temperature in 90 minutes. After centrifugation, the BSA-compound 17 conjugation product is purified by gel filtration (Sephadex G25) eluting with PBS (pH 7.2), collecting fractions having a volume of ca. 1 ml.

The conjugation product, visible due to its green-blue colour, is obtained from the second fraction to the fourth one. The labelling ratio has been determined spectrophotometrically measuring the protein concentration and the number of moles of the compound 17 per mole of BSA.

In the practiced experimental conditions the labelling ratio resulted comprised between 4 and 5 and may be adjusted by variation of the initial reagents ratio, according to the needs.

Analogously, conjugates of the other formula (I) compounds according to the invention can be prepared.

Pharmaceutical Formulations

Therapeutic compositions containing the compounds of the present invention include solutions also for the administration by parenteral injection route, preparations for topical application, etc.

The topical formulations according to the invention are for example lotions, creams, ointments or gels. Particularly preferred are DMSO or Azone aqueous solutions, up to 50%.

The formula (I) compounds of the present invention having lipophilic characteristics may be incorporated in liposomes or microcapsules and used in this form for both types of application mentioned above.

The dosages normally range from 0.1 to 20 mg of compound of formula (I) per kilogram of body weight, preferably 0.2-5 mg/Kg of body weight.

Biocidal Activity

The compounds disclosed in the present invention for the applications according to PDT show many advantages, such as the very low toxicity in the absence of light.

Each molecule can be repeatedly excited, with the consequent production of singlet oxygen or other reactive species by a continuous process.

Due to their short lifetime, they hit the target cell without possibility of diffusion to vicinal cells: singlet oxygen is produced only in the pathologic site, and the portion that does not react with the biological target undergoes a rapid decay.

These characteristics are further improved by the specific localisation of the photosensitising agent, by the nature of the photosensitizer itself or guaranteed by a suitable carrier. The photodynamic therapy that uses the present compounds is therefore selective and does not allow for systemic or dermal phototoxicity.

The production of singlet oxygen occurs only simultaneously with irradiation and stops immediately as soon as the irradiation is interrupted.

The light sources suitable for carrying out the PDT are well known in the art and comprise properly filtered non coherent white light or laser light having the required specific wavelength preferably ranging from 650 to 750 nm.

The total amount of radiation applied varies according to the treatment and the localisation of the tissues to be treated.

The amount of radiation ranges usually from 50 to 1000 $J/cm^2$, and preferably from 100 to 350 $J/cm^2$.

Antifungal and Antibacterial (Gram-Positive E Gram-Negative) Activity

The compounds synthesized have been assayed for their antifungal and antibacterial (Gram-positive e Gram-negative) activity. For the experiments the following micro-organisms were used: *Candida albicans* (ATCC10231; yeast), *Staphylococcus aureus* (ATCC 6538P, MRSA; Gram-positive), *Escherichia coli* (04; Gram-negative). All the micro-organisms were used in the experiments in a stationary state of growth. An example of experimental protocol used to assess the photoinactivation of micro-organisms is described as follows.

Cells in a stationary state of growth have been washed in physiological buffered saline solution (PBS) and diluted in order to obtain a cell suspension in the range $10^6 \div 10^9$ cells/ml in PBS or appropriate medium.

Cell suspensions have then been treated with scalar aliquots of the photosensitising agent to be tested in the range 30÷0.01 µM, eventually as a photosensitizer conjugate. Cells have been Incubated in the dark at 37° C. for 1 hour, eventually washed at the end with PBS then irradiated with red light (700±30 nm; 10÷100 $mW/cm^2$; 1÷30 minutes). In order to determine the percentage of cell population after photoinactivation for each photosensitizer concentration, serially diluted samples resulting from the irradiation have been plated on Sabouraud Dextrose Agar (*C. Albicans*), on Tryptic Soy Agar (*S. aureus*), or on other suitable culture media and the data were compared with dark controls.

Examples of microbial photoinactivation by using some compounds of the present invention are given in the figures.

Figure 1:
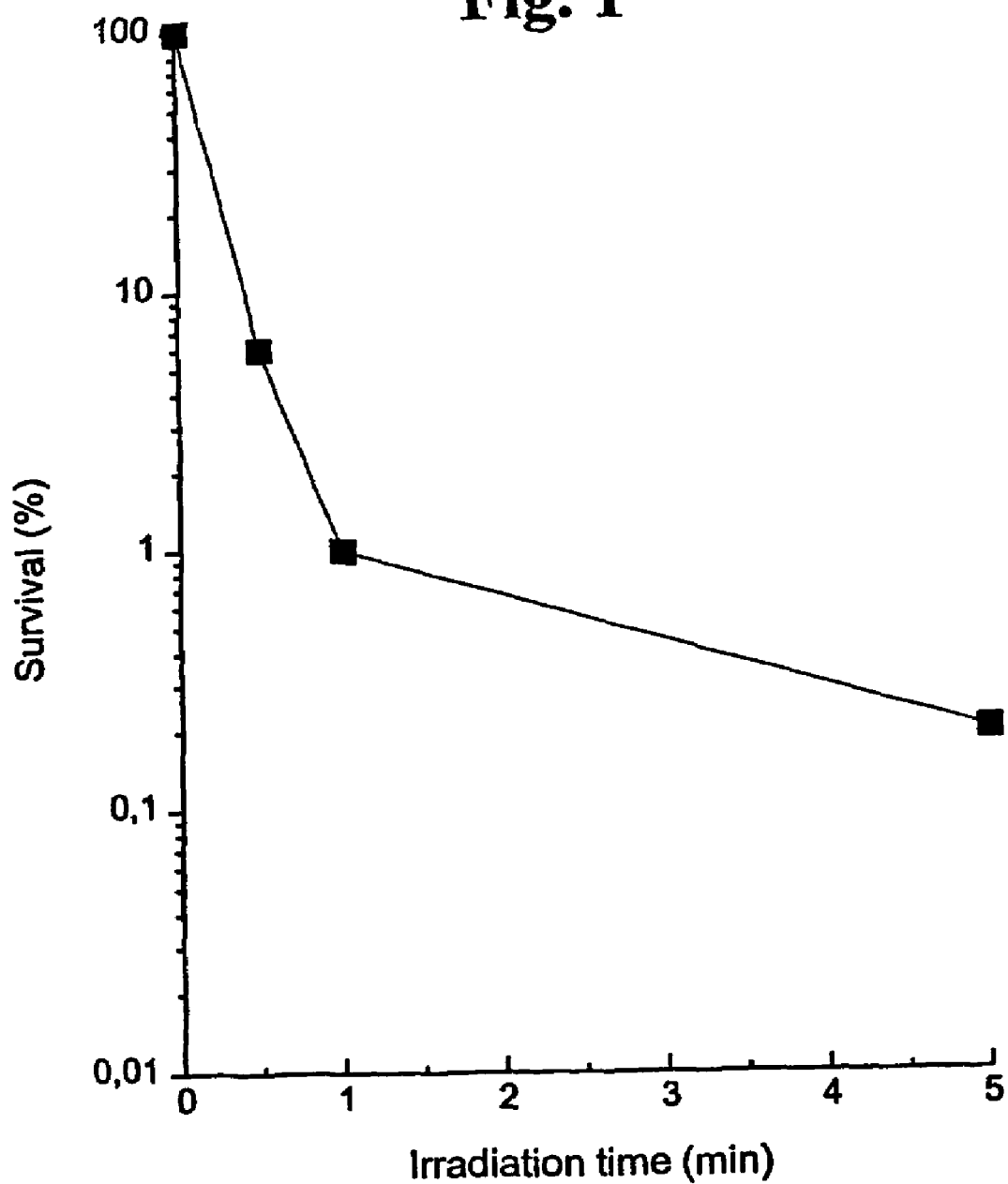
FIG. 1: survival (%) vs. irradiation time (min.) with red light at 100 mW/cm$^2$ for *E. coli* 04 previously incubated for 5 min. with 2.5 μM of compound 18.

FIG. 1 shows the variation of the percentage survival as a function of irradiation time (administered light dose) for *E. coli* 04 previously incubated for 5 min. with 2.5 µM of compound 18 prepared as described in Example 3, then irradiated with red light at 100 $mW/cm^2$.

Figure 2:
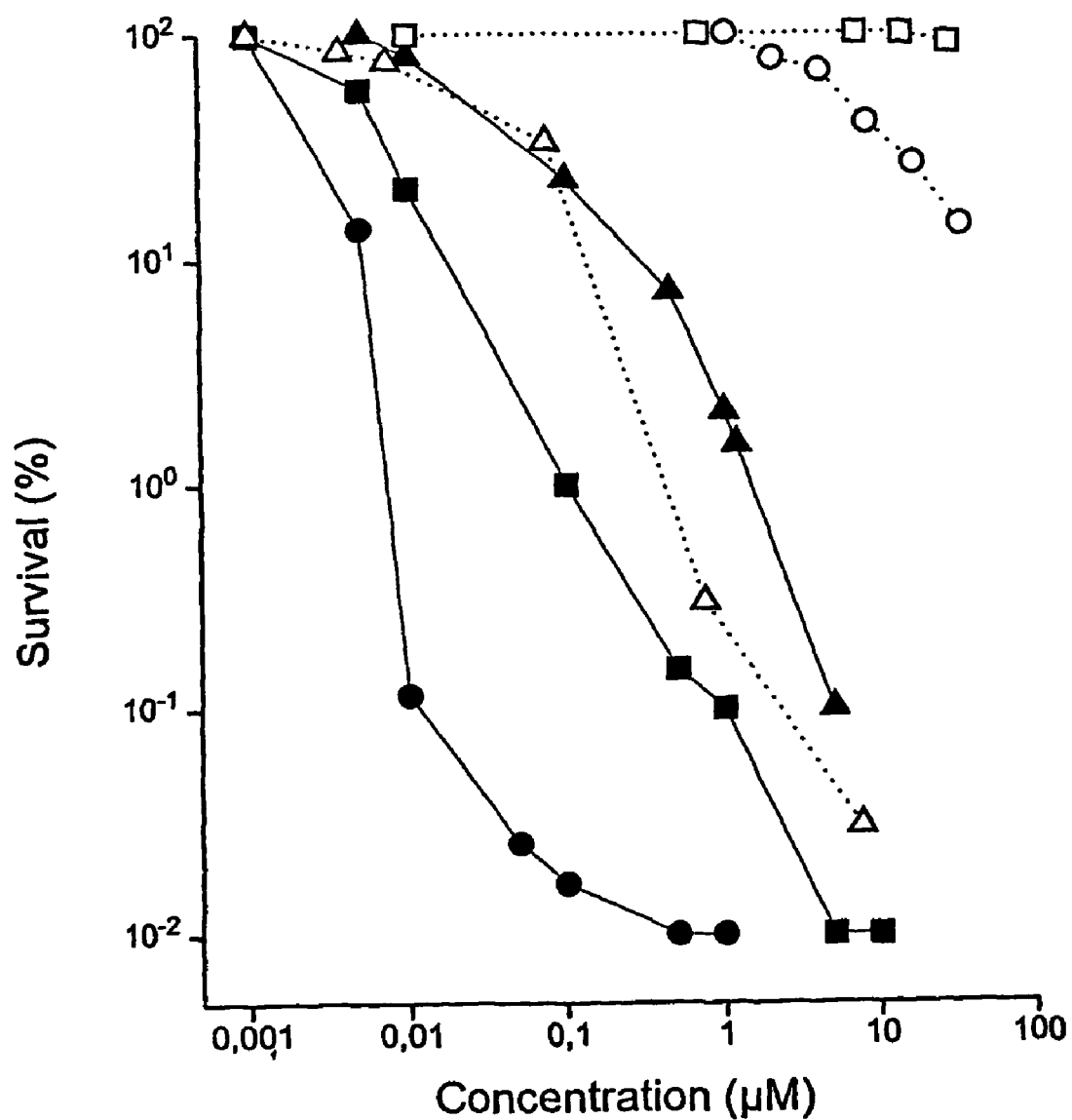
FIG. 2: survival (%) of the colony forming units (CFU) of *Candida albicans* vs. concentration (μM) of the following compounds according to the invention, in comparison with structurally similar compounds previously cited in literature.

FIG. 2 accounts for the decrease of the colony forming units (CFU) of *Candida albicans* after treatment with different concentrations of some compounds described in this invention, in comparison with structurally similar compounds previously cited in literature.

Reported in FIG. 3 is the variation of CFU as a function of administered light dose for various concentrations of *Candida albicans* cells, incubated for 60 min with 1 µM of the compound 19 then irradiated with 100 $mW/cm^2$ red light.

Finally we report in the following Table 1 the survival of 3T3 cells as a model of mammalian cells as well as on some micro-organisms after photodynamic treatment with the compound 18 prepared as described in Example 3 in PBS+ 5% DMSO, as an example to demonstrate the selectivity and efficacy of the described compounds. The irradiation is carried out with red light (650-750 nm), 50 $mW/cm^2$.

TABLE 1

| Cells or micro-organisms | Survival (%) | | | |
| --- | --- | --- | --- | --- |
| | Irradiation 1 min. | | Irradiation 5 min. | |
| | 1 µM | 10 µM | 1 µM | 10 µM |
| *3T3 | 100 | 100 | 97 | 94 |
| *S. aureus (MRSA) | 0.0002 | 0.0001 | 0.0001 | 0.0001 |
| *E. coli | 100 | 100 | 100 | 2.34 |
| **C. albicans | 0.0001 | N.D. | 0.0001 | N.D. |

*5 min. of pre-incubation
**10 min. of pre-incubation

Evidence about selectivity is also supported by experiments on the haemolytic properties of the above described compounds. In the following Table 2 it is shown that several compounds are not toxic for the erythrocytes as well: in fact no haemolysis is detected after treatment and irradiation by using photosensitzer concentrations well above the ones needed for the complete inactivation of micro-organisms. These findings strengthen the usefulness of the described compounds and enable them to be used even for the blood and blood derivatives sterlisation.

TABLE 2

| Compound | Concentration (µM) | % Haemolysis (Dark treatment) | % Haemolysis (Light treatment) 30 $J/cm^2$ (50 $mW/cm^2$ × 10 min) |
| --- | --- | --- | --- |
| 4 | 5 | 1.5 | 1.5 |
| | 1 | 1.5 | 1.2 |
| | 0.5 | 4.7 | 0.9 |
| 19 | 5 | 7.6 | 0.6 |
| | 1 | 5.0 | 2.0 |
| | 0.5 | 0.8 | 0.6 |
| | 0.05 | 4.0 | 0.5 |

TABLE 2-continued

| Compound | Concentration (μM) | % Haemolysis (Dark treatment) | % Haemolysis (Light treatment) 30 J/cm$^2$ (50 mW/cm$^2$ × 10 min) |
|---|---|---|---|
| 26 | 1 | 6.3 | 5.0 |
|  | 0.5 | 1.2 | 0.6 |
| Compound 42 disclosed in EP-A- No. 98115036.0 | 0.5 | 2.8 | 3.2 |
|  | 0.1 | 1.1 | 2.0 |
|  | 0.05 | 0.9 | 0.6 |

The invention claimed is:

1. A therapeutic method for the treatment of fungal or bacterial pathological conditions, which comprises administering to a subject in a need of such a treatment a therapeutically effective amount of a pharmaceutical composition containing as active ingredient a compound of general formula (I)

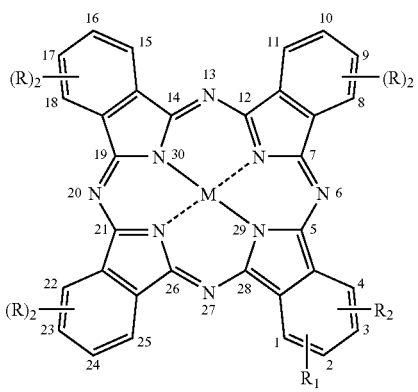

or a conjugate of a compound of general formula (I) with a macromolecule selected from the group consisting of aminoacids, polypeptides, proteins and polysaccharides, optionally in combination with pharmaceutically acceptable excipients, in which general formula (I):

M is selected from the group consisting of Zn, Si(OR$_8$)$_2$, Ge(OR$_8$)$_2$ and AlOR$_8$;

R is H or a group selected from alkyl, alkenyl and alkyloxy group, linear or branched, having from 1 to 10 carbon atoms provided that, when R is different from H, the positions 8, 11, 15, 18, 22, 25 or 9, 10, 16, 17, 23, 24 are substituted; and R$_1$ and R$_2$, equal or different from one another, are H or a group (X)$_p$R$_3$, wherein X is selected from the group consisting of O, S, —NR$_6$ and —CH$_2$—; and R$_3$ is

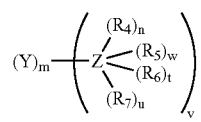

where:

Y is selected from the group consisting of C1-C10 alkyl and phenyl, optionally substituted, or it forms with the Z group, to which it is bound, a saturated or unsaturated heterocycle, optionally substituted, which may contain up to two heteroatoms selected from the group consisting of N, O and S;

Z is selected from the group consisting of —N, —CH$_2$N and —CONHCH$_2$CH$_2$N;

R$_4$ and R$_5$, equal or different from one another, are selected from the group consisting of C1-C15 alkyl and phenyl, or form with the Z group, to which they are bound, a saturated or unsaturated heterocycle, optionally substituted, which may contain up to two heteroatoms selected from the group consisting of N, O and S;

R$_6$ and R$_7$, equal or different from one another, are selected from the group consisting of H and C1-C15 alkyl;

m, n, p, w, t and u, independently from one another, are 0 or 1; and v is an integer between 1 and 3, provided that when R$_1$ and R$_2$ are the same, they are not H and are in the positions 1,4 or 2,3, whereas, when only one between R$_1$ and R$_2$ is different from H, the position 1 or 2 is substituted, or R$_1$ and R$_2$, taken together, form a saturated or unsaturated heterocycle, possibly substituted, which may contain up to two heteroatoms selected from the group consisting of N, O and S;

R$_8$ is selected from H and C1-C15 alkyl.

2. The therapeutic method according to claim 1, wherein M is Zn.

3. The therapeutic method according to claim 1, wherein said saturated or unsaturated heterocycle is selected from the group consisting of morpholine, piperidine, pyridine, pyrimidine, piperazine, pyrrolidine, pyrroline, imidazole, aniline and julolidine.

4. The therapeutic method according to claim 1, wherein the said group (X)$_p$R$_3$ contains substituents bearing tertiary or quaternary nitrogen.

5. The therapeutic method according to claim 4, wherein the said group (X)$_p$R$_3$ is selected from the group consisting of:

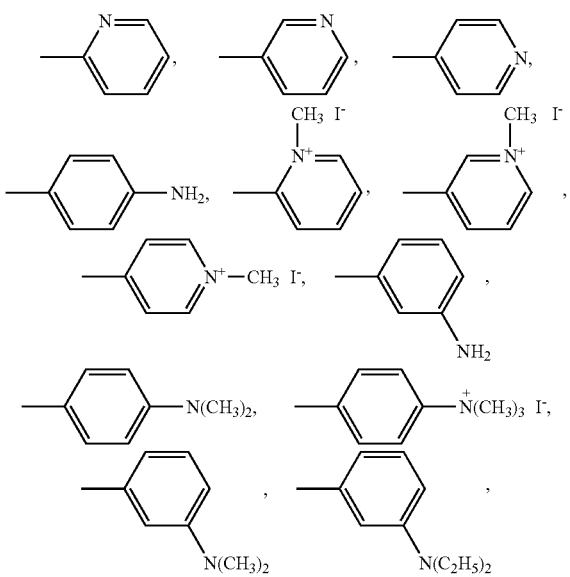

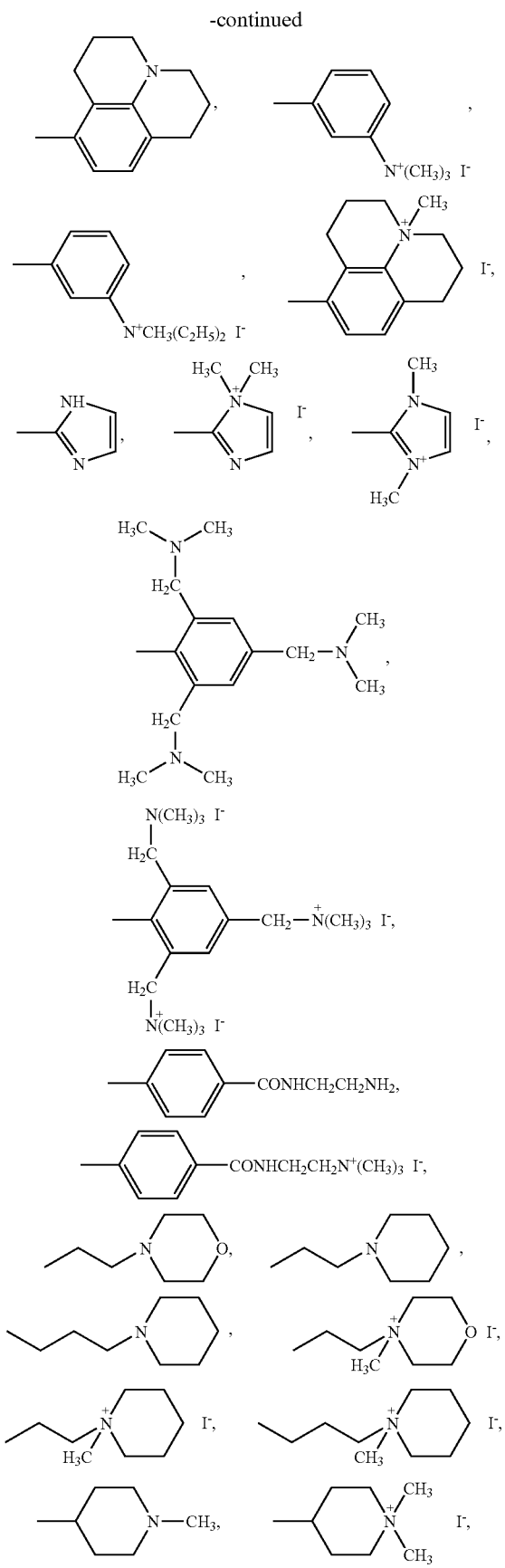

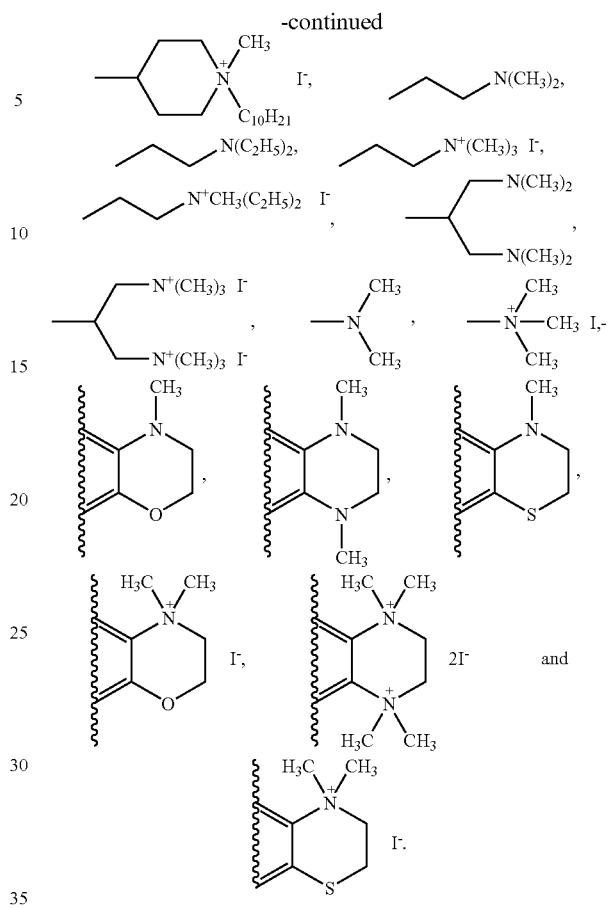

6. The therapeutic method according to claim 1, wherein in said compounds of general formula (I):

$R=R_2=H$, and $R_1=$1,3-bis-(dimethylamino)2-propyloxy in position 2 (Compound 1);

$R==H$, and $R_1=$pyridin-4-yl-oxy in position 2 (Compound 2);

$R==H$, and $R_1=$3-(dimethylamino)phenoxy in position 2 (Compound 3);

$R==H$, and $R_1=$1-methylpiperidin-4-yl-oxy in position 2 (Compound 4);

$R=H$, and $R_1=R_2=$pyridin-4-yl-oxy in positions 2, and 3 (Compound 5);

$R=R_2=H$, and $R_1=$1,3-bis-(dimethylamino)-2-propyloxy in position 1 (Compound 6);

$R=H$, and $R_1=R_2=$3-(piperidin-1yl)propyloxy in positions 1, and 4 (Compound 7);

$R=H$, and $R_1=R_2=$3-(dimethylamino)phenoxy in positions 2, and 3 (Compound 8);

$R==H$, and $R_1=$pyridin-2-yl-oxy in position 2 (Compound 9);

$R==H$, and $R_1=$pyridin-3-yl-oxy in position 2 (Compound 10);

$R=R_2=H$, and $R_1=$3-(dimethylamino)phenoxy in position 1 (Compound 11);

$R=H$, and $R_1=R_2=$2-(diethylamino)ethylthio in the positions 2, and 3 (Compound 12);

$R=H$, and $R_1=R_2=$pyridin-3-yl-oxy in positions 2, and 3 (Compound 13);

$R==H$, and $R_1=$2-(dimethylamino)ethyloxy in position 1 (Compound 14);

R==H, and $R_1$=2-(piperidin-1-yl)ethyloxy in position 1 (Compound 15);

R==H, and $R_1$=2-(piperidin-1-yl)ethyloxy in position 2 (Compound 16);

R=$R_2$=H, and $R_1$=N-(2-aminoethyl)benzamidoyl-4-oxy trifluoro acetate (Compound 17);

R=$R_2$=H, and $R_1$=1,3-bis-(trimethylammonium)-2-propyloxy diiodide in position 2 (Compound 18);

R=$R_2$=H, and $R_1$=3-(trimethylammonium)phenoxy iodide in position 2 (Compound 19);

R=$R_2$=H, and $R_1$=1,1-dimethylpiperidinium-4-yl-oxy iodide in position 2 (Compound 20);

R=H, and $R_1$=$R_2$=3-(1-methylpiperidinium-1-yl)propyloxy iodide in positions 1, and 4 (Compound 21);

R=H, and $R_1$=$R_2$=3-(trimethylammonium)phenoxy iodide in positions 2, and 3 (Compound 22);

R=$R_2$=H, and $R_1$=1,3-bis-(trimethylammonium)-2-propyloxy diiodide in position 1 (Compound 23);

R=$R_2$=H, and $R_1$=3-(trimethylammonium)phenoxy iodide in position 1 (Compound 24);

R=H, and $R_1$=$R_2$=2-(diethylmethylammonium)ethylthio iodide in positions 2 and 3, (Compound 25); and R==H, and $R_1$=1-methylpyridinium-4-yl-oxy in position 2 (Compound 26).

7. The therapeutic method according to claim 1, wherein said pharmaceutical composition contains said compound of general formula (I) incorporated in liposomes or microcapsules.

8. The therapeutic method according to claim 1, wherein said pharmaceutical composition is in the form of solutions for the administration by parenteral route or of preparations for topical administration.

9. The therapeutic method according to claim 8, wherein said preparations for topical administration are selected from lotions, creams, ointments or gels.

10. The therapeutic method according to claim 8, wherein said solutions are DMSO aqueous solutions, up to 5000.

11. The therapeutic method according to claim 1, further comprising the irradiation of the tissue to be treated with a light source suitable for carrying out the photodynamic therapy (PDT).

12. The therapeutic method according to claim 11, wherein said light source is selected from properly filtered white light and laser light having wavelength ranging from 650 to 750 nm.

* * * * *